United States Patent
Lee

(10) Patent No.: US 11,044,957 B2
(45) Date of Patent: Jun. 29, 2021

(54) WRIST GUARD

(71) Applicant: Sang Jin Lee, Gyeongsangnam-do (KR)

(72) Inventor: Sang Jin Lee, Gyeongsangnam-do (KR)

( * ) Notice: Subject to any disclaimer, the term of this patent is extended or adjusted under 35 U.S.C. 154(b) by 0 days.

(21) Appl. No.: 16/348,145

(22) PCT Filed: Sep. 15, 2017

(86) PCT No.: PCT/KR2017/010137
§ 371 (c)(1),
(2) Date: May 7, 2019

(87) PCT Pub. No.: WO2018/088686
PCT Pub. Date: May 17, 2018

(65) Prior Publication Data
US 2019/0364991 A1    Dec. 5, 2019

(30) Foreign Application Priority Data
Nov. 8, 2016  (KR) .......................... 10-2016-0148362

(51) Int. Cl.
*A41D 13/08* (2006.01)
*A41D 20/00* (2006.01)
(Continued)

(52) U.S. Cl.
CPC ........... *A41D 13/088* (2013.01); *A41D 20/00* (2013.01); *A41D 13/081* (2013.01);
(Continued)

(58) Field of Classification Search
CPC .. A41D 13/088; A41D 13/082; A41D 13/081; A41D 20/00; A41D 2400/32; A61F 5/05866; A61F 5/30
(Continued)

(56) References Cited

U.S. PATENT DOCUMENTS 1,221,513 A * 4/1917 Coyne ................... A41D 20/00
                                                         2/170
4,244,057 A * 1/1981 Burnham ........... A41D 19/0024
                                                         2/160
(Continued)

FOREIGN PATENT DOCUMENTS

CN    101878970    11/2010
CN    104768413    7/2015
(Continued)

OTHER PUBLICATIONS

International Search Report for PCT/KR2017/010137 dated Dec. 22, 2017 and its English translation from WIPO (now published as WO 2018/088686).
(Continued)

*Primary Examiner* — Khaled Annis
*Assistant Examiner* — Dakota Marin
(74) *Attorney, Agent, or Firm* — Revolution IP, PLLC

(57) ABSTRACT

The present invention relates to a wrist guard and provides a wrist guard that does not pressurize the entire wrist portion but allows for pressurizing only the radius portion and the ulna portion, thereby not only performing a wrist protection function in a stable manner, but also not hindering blood circulation since other portions of the wrist are not pressurized, and thus may be conveniently used since side-effects such as hand numbness or hand swelling do not occur even when wearing same for a long period, and the position and thickness of a pressurizing pad for pressurizing the radius portion and the ulna portion of the wrist may be adjusted according to the needs of a user, and thus the wrist guard may be more conveniently used since same may be altered into an optimal state according to physical conditions of the user or environmental conditions.

13 Claims, 7 Drawing Sheets

(51) Int. Cl.
    *A61F 5/50*      (2006.01)
    *A61F 5/058*     (2006.01)
(52) U.S. Cl.
    CPC ........ *A41D 13/082* (2013.01); *A41D 2400/32* (2013.01); *A61F 5/05866* (2013.01); *A61F 5/50* (2013.01)
(58) Field of Classification Search
    USPC .............................................................. 2/16
    See application file for complete search history.

(56) References Cited

U.S. PATENT DOCUMENTS

| | | | | |
|---|---|---|---|---|
| 4,977,625 | A * | 12/1990 | Charters, III | A41D 13/088 2/16 |
| 5,921,949 | A | 7/1999 | Dray | |
| 6,120,472 | A | 9/2000 | Singer, Jr. | |
| 6,328,706 | B1 * | 12/2001 | Yattavong | A61F 5/05866 128/878 |
| 8,641,650 | B2 * | 2/2014 | Spitzer | A61F 5/0118 602/21 |
| 9,474,310 | B2 * | 10/2016 | Khuong | A41D 13/088 |
| 10,390,839 | B2 * | 8/2019 | Benz | A61B 17/135 |
| 10,537,149 | B2 * | 1/2020 | Cormier | A42B 3/124 |
| 2004/0049141 | A1 * | 3/2004 | Slautterback | A61F 5/0118 602/21 |
| 2007/0142883 | A1 * | 6/2007 | Quincy, III | A61F 7/034 607/96 |
| 2009/0205106 | A1 * | 8/2009 | Sohn | A63B 21/0602 2/170 |
| 2015/0290018 | A1 * | 10/2015 | Okazawa | A63B 69/0059 428/138 |
| 2017/0181882 | A1 * | 6/2017 | Chisena | A61F 5/05833 |

FOREIGN PATENT DOCUMENTS

| | | |
|---|---|---|
| JP | 2003-061995 | 3/2003 |
| JP | 2006-288484 | 10/2006 |
| JP | 5894204 | 3/2016 |
| KR | 10-2000-0074622 | 12/2000 |
| KR | 20-0385773 | 6/2005 |
| KR | 10-2005-0100081 | 10/2005 |

OTHER PUBLICATIONS

Written Opinion of the International Searching Authority for PCT/KR2017/010137 dated Dec. 22, 2017 and its English translation by Google Translate (now published as WO 2018/088686).

Extended European Search Report dated Sep. 26, 2019 for European Application No. 17870384.9.

Office Action dated Apr. 3, 2020 for Chinese Patent Application No. 201780068617.9 and its English translation provided by Applicant's foreign counsel.

International Preliminary Report on Patentability (Chapter I) for PCT/KR2017/010137 dated May 14, 2019 and its English translation from WIPO.

* cited by examiner

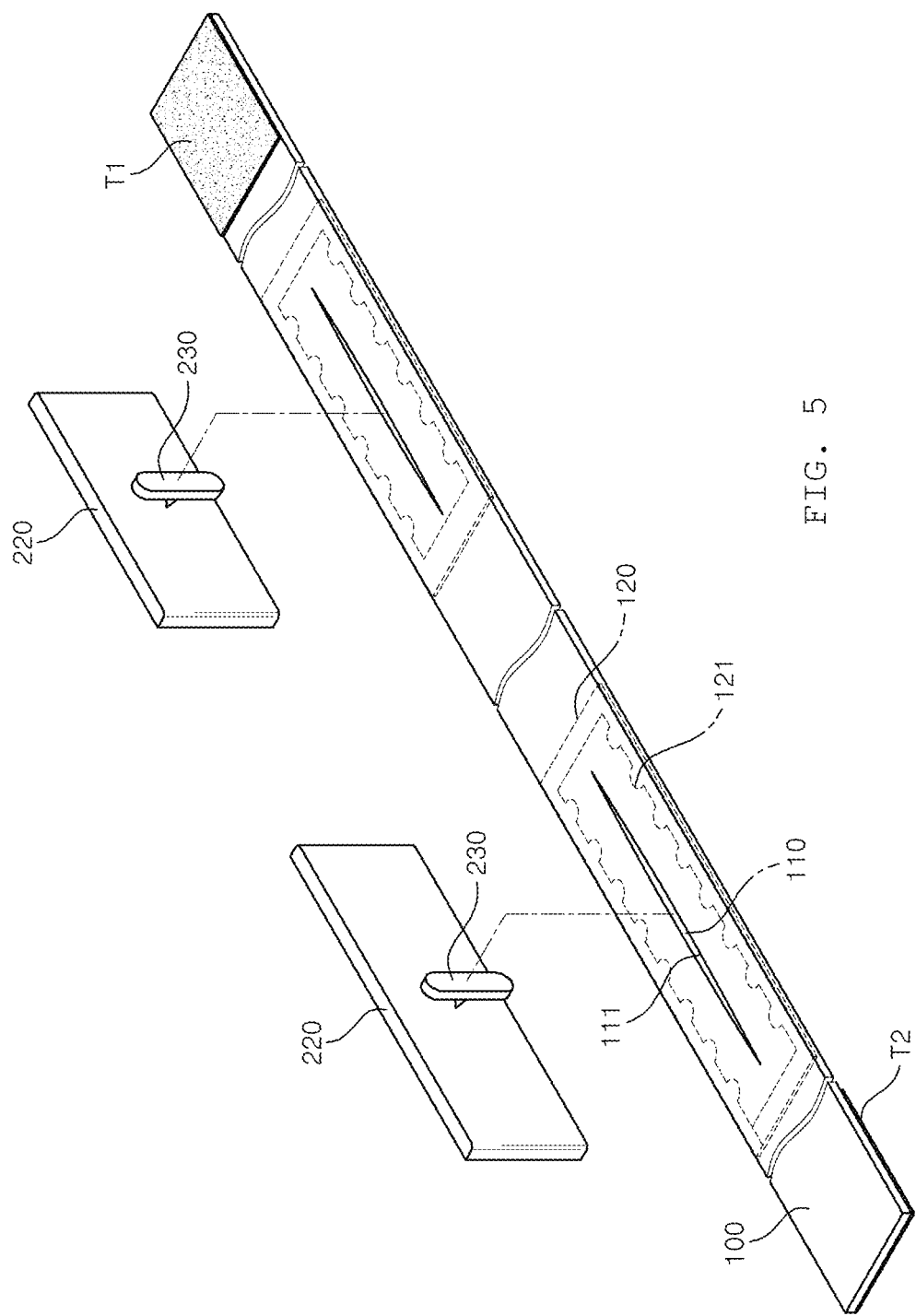

WRIST GUARD

CROSS-REFERENCE TO RELATED APPLICATIONS

This application is the U.S. National Stage of International Patent Application No. PCT/KR2017/010137 filed on Sep. 15, 2017, which claims the priority to Korean Patent Application No. 10-2016-0148362 filed in the Korean Intellectual Property Office on Nov. 8, 2016, the entire contents of which are incorporated herein by reference.

TECHNICAL FIELD

The present disclosure relates to a wrist guard. More particularly, the present disclosure relates to a wrist guard that allows only the radial part and the ulnar part (of the wrist) to be pressurized without allowing the entire wrist portion (of the arm) to be pressurized. The wrist guard may perform a wrist protection function in a reliable manner without hindering blood circulation, since other portions of the wrist are not pressurized. The wrist guard may be conveniently used, since side-effects such as hand numbness or hand swelling do not occur, even when the wrist guard is worn for an extended period of time. In addition, the wrist guard allows the position and thickness of a pressurizing pad for pressurizing the radial part and the ulnar part of the wrist to be adjusted according to the needs of a user. Since the wrist guard may be altered to have an optimal state according to physical condition of the user or environmental conditions, the wrist guard may be more conveniently used.

BACKGROUND ART

The arm (and hand) of the human body has a forearm, comprising the radial part and the ulnar part, a wrist, comprising eight carpalia, a palm comprising five metacarpal joints that enable rotation, flexion, and extension, and fingers comprising a plurality of phalanx bones that enables an object to be held.

These joints can suffer injury, due to repetitive and continuous strain during exercise or an activity carried out by hand, and at the time of injury, healing may not be complete and pain can be continuously suffered.

M Accordingly, a wrist guard for protecting the joints and bones by being worn on the wrist of the body has been devised and used.

In general, like other body guards such as ankle guards, wrist guards are worn on the wrist to protect the soft joints of the wrist. Such wrist guards may be worn by athletes who play various sports, workers who do a physical job, or children who enjoy playing, for the safety thereof.

Conventional wrist guards are provided in the form of a band that wraps around the wrist so that the wrist portion (of the arm) is evenly compressed along the circumference thereof. This wrist compression serves to protect the wrist joints and prevent excessive wrist bending.

However, since conventional wrist guards compress the wrist evenly over the entire area thereof, when such wrist guards are worn for an extended period of time, blood flow in the wrist artery may not be smooth, causing hand numbness or swelling of the hand. Because of the same inconvenience, a user may tend to remove or may not wear such a wrist guard at all, so that the use of such a wrist guard is not very effective. As a result, the wrist may not be safely protected during various types of exercise and activities, and thus it may be vulnerable to injury.

DISCLOSURE

Technical Problem

Accordingly, the present disclosure has been made in consideration of the above-described problems occurring in the related art, and an object of the present disclosure is to provide a wrist guard capable of compressing only a specific area of the wrist rather than the whole area thereof, so as not to interfere with blood circulation by allowing the remaining part of the wrist to remain uncompressed. The wrist guard can be conveniently used without causing side effects such as hand numbness and swelling of the hands, even when worn for a long period of time, and thus the usability thereof can be improved.

Another object of the present disclosure is to provide a wrist guard capable of compressing only the radial part and the ulnar part of the wrist in the direction of the center of the wrist using a compression pad, thereby preventing the occurrence of side effects such as numbness and swelling of the hand, as well as effectively complementing the attachment to the wrist, so that a wrist protection function of preventing excessive bending of the wrist and alleviating wrist pain can be reliably performed.

WA A further object of the present disclosure is to provide a wrist guard capable of being used more conveniently by adjusting the position and thickness of a compression pad for compressing the radial part and the ulnar part of the wrist to the optimum state, according to the user's physical condition or environmental condition.

Technical Solution

The present disclosure provides a wrist guard for being worn on the wrist to protect the wrist, the wrist guard including: a band body configured to be worn on the wrist by encircling the wrist; and a pair of compression pads disposed on opposite portions of the band body worn on the wrist to respectively compress a part of the wrist, such that a portion of the wrist other than those compressed by the compression pads is not compressed.

The compression pads may include a radial compression pad mounted on one portion of the band body to compress the radial part of the wrist and an ulnar compression pad mounted on the other portion of the band body to compress the ulnar part of the wrist.

The radial compression pad may have a length L1 longer than a length L2 of the ulnar compression pad.

At least one of the radial compression pad and the ulnar compression pad may have a concave surface to be in contact with the wrist in a longitudinally intermediate portion thereof.

The compression pads may be mounted to be movable in a longitudinal direction of the band body.

A contact surface of the compression pad with the band body may be provided with an insertion protrusion, and the band body may be provided with a pad receiving section in which the insertion protrusion is inserted and movable, the pad receiving section internally having a movement guide part along which the insertion protrusion is forcedly movable in a state of being engaged therewith.

The radial compression pad and the ulnar compression pad may respectively further include a separate auxiliary compression pad detachably attached to a contact surface thereof with the wrist.

The contact surface of the radial compression pad and the ulnar compression pad may be provided with a coupling groove, and the auxiliary compression pad may be provided on one portion thereof with a coupling protrusion to be inserted into and engaged with the coupling groove, so that the auxiliary compression pads are detachably attached to the radial compression pad and the ulnar compression pad, respectively, by the engagement between the coupling groove and the coupling protrusion.

The coupling groove may be provided with a plurality of coupling grooves in the longitudinal direction of the radial compression pad and the ulnar compression pad to adjust an engagement position of the auxiliary compression pads with the radial compression pad and the ulnar compression pad.

The compression pads may be formed from a leather or silicone material.

The compression pads may be further provided with a health aid to be inserted into the compression pads, the health aid being formed of zirconium or germanium.

The band body may be provided in the form of an elastic ring band, or a band fixedly formed into a ring type by means of a fastener.

Advantageous Effects

As set forth above, the wrist guard is capable of compressing only a specific area of the wrist rather than the whole area thereof, so that the remaining part of the wrist is not compressed, which does not interfere with blood circulation, thereby facilitating convenient use without side effects such as hand numbness and swelling of the hands, even when worn for a long period of time, and thus improving usability.

Further, the wrist guard is capable of compressing only the radial part and the ulnar part of the wrist in the direction of the center of the wrist using a compression pad, thereby preventing the occurrence of side effects such as numbness and swelling of the hand, as well as effectively complementing the attachment to the wrist to reliably perform a wrist protection function to prevent excessive bending of the wrist and alleviate wrist pain.

Still further, the wrist guard is capable of being used more conveniently by adjusting the position and thickness of a compression pad for compressing the radial part and the ulnar part of the wrist to the optimum state, according to a user's physical condition or environmental condition.

DESCRIPTION OF DRAWINGS

FIGS. 5 and 6 are views schematically illustrating a structure of the compression pad moving along the band body according to an exemplary embodiment of the present disclosure.

MODE FOR INVENTION

Figure 1:
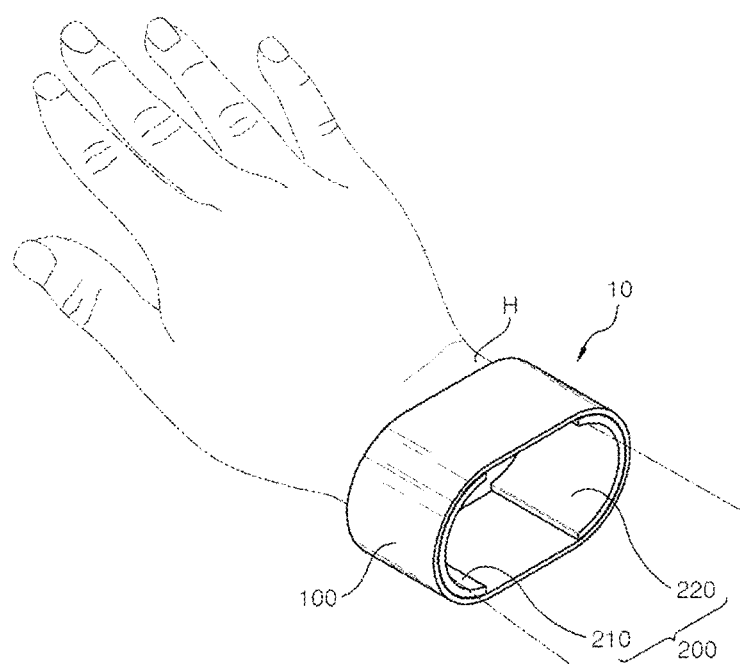
FIG. 1 is a perspective view schematically illustrating a wrist guard according to an exemplary embodiment of the present disclosure.

Hereinafter, exemplary embodiments of the present disclosure will be described in detail with reference to the accompanying drawings. Throughout this document, reference should be made to the drawings, in which the same reference numerals and symbols will be used to designate the same or like components. In the following description of the present disclosure, detailed descriptions of known functions and components incorporated herein will be omitted in the case that the subject matter of the present disclosure may be rendered unclear thereby.

Figure 2:
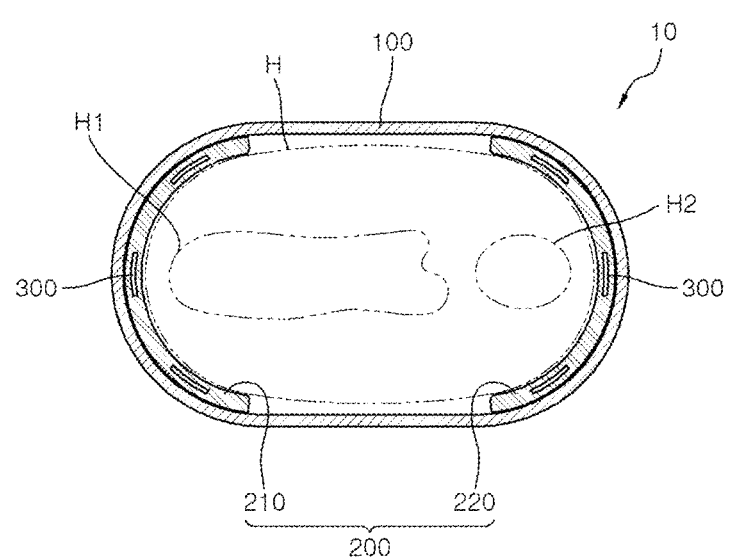
FIG. 2 is a cross-sectional view schematically illustrating a structure of the wrist guard according to the exemplary embodiment of the present disclosure.
Figure 3A:
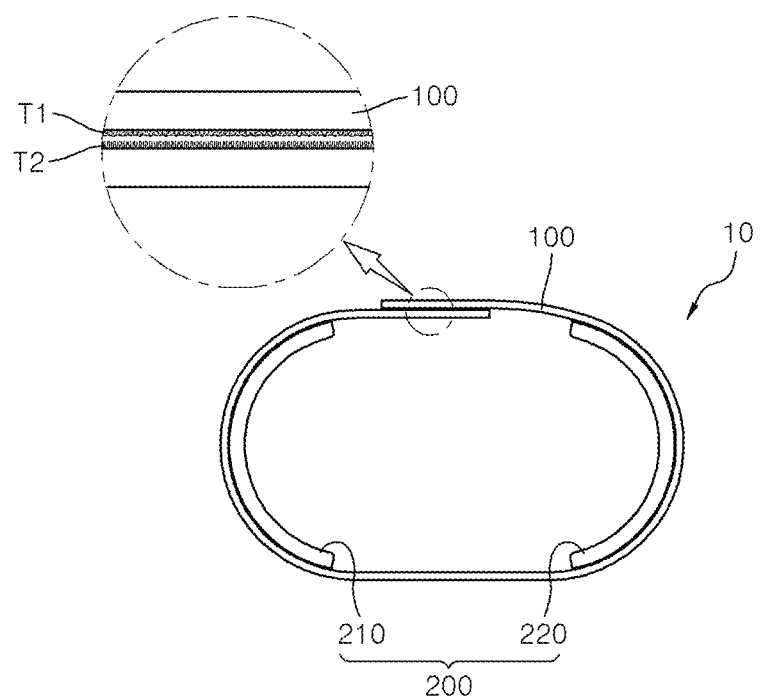
FIGS. 3A and 3B are schematic views illustrating various forms of a band body of the wrist guard according to an exemplary embodiment of the present disclosure.
Figure 3B:
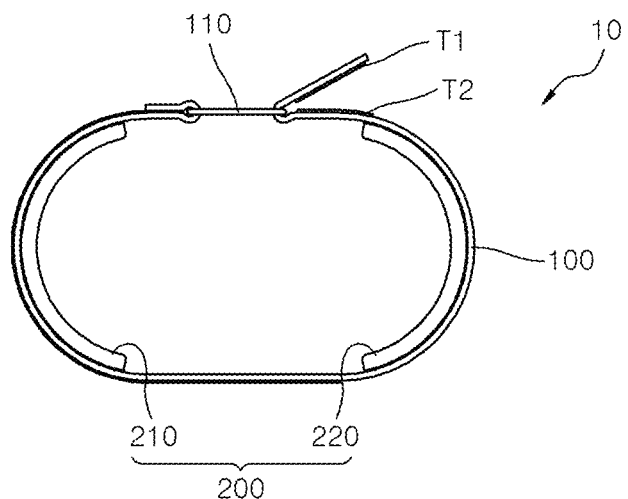
Figure 4A:
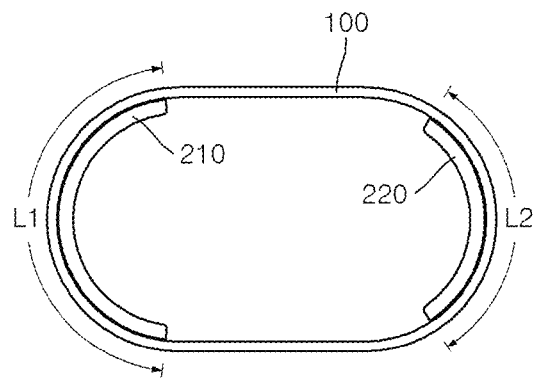
FIGS. 4A, 4B, and 4C are schematic views illustrating various forms of a compression pad of the wrist guard according to an exemplary embodiment of the present disclosure.
Figure 4B:
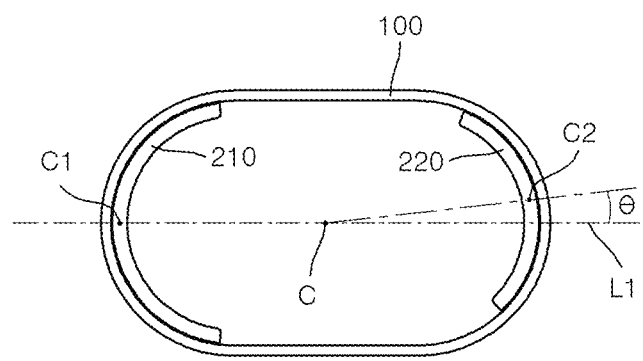
Figure 4C:
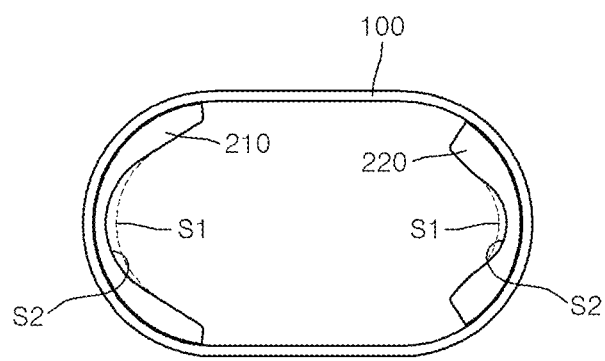

FIG. 1 is a perspective view schematically illustrating a wrist guard according to an exemplary embodiment of the present disclosure; FIG. 2 is a cross-sectional view schematically illustrating a structure of the wrist guard according to the exemplary embodiment of the present disclosure; FIGS. 3A and 3B are schematic views illustrating various forms of a band body of the wrist guard according to an exemplary embodiment of the present disclosure; and FIGS. 4A, 4B, and 4C are schematic views illustrating various forms of a compression pad of the wrist guard according to an exemplary embodiment of the present disclosure.

The wrist guard 10 according to an exemplary embodiment of the present disclosure is worn on the wrist H of the user to reliably protect the wrist without side effects such as hand numbness. The wrist guard 10 includes a band body 100 and compression pads 200.

The band body 100 is worn on the wrist H by encircling the wrist H. The band body 100 may be provided in various forms that can be worn on the wrist H. For example, the band body may be provided in the form of a simple ring-shaped elastic band as illustrated in FIGS. 1 and 2, or may be provided in the form of a band which is fixedly formed into a ring shape by means of a separate fastener such as Velcro T1, T2 as illustrated in FIG. 3. In this case, the band may be formed from a fabric.

In the case in which the band body 100 is provided in a simple band shape, as illustrated in FIG. 3A, the band body may be provided on both ends thereof with male and female Velcro parts T2 and T1, respectively, which are fastened together to form the band body into a ring shape. Due to this configuration, the length of the band body is adjustable by a user. Alternatively, as illustrated in FIG. 3B, the band body 100 may be provided with a strap loop 110 on one end thereof and male and female Velcro parts T2 and T1 on the other end thereof, such that the male and female Velcro parts T2 and T1 are fastened together while holding the strap loop 110, thereby forming the band body into a ring shape.

Of course, the band body 100 may be provided in various forms that are wearable on the wrist, in addition to the above-described configurations.

The compression pads 200 are disposed on opposite portions of the band body 100 worn on the wrist H to respectively compress a portion of the wrist H. The compression pads 200 may be formed of a soft material such as a leather material or a silicone material so as to be in close contact with the wrist H and may be provided in a pad shape having a predetermined thickness so as to be able to compress a portion of the wrist H.

The compression pads 200 may include a radial compression pad 210 mounted on one portion of the band body 100 to compress the radial part H1 of the wrist H, and an ulnar compression pad 220 mounted on the other side of the band body 100 to compress the ulnar part H2 of the wrist H.

According to this configuration, the wrist guard 10 is constructed in such a manner that, in a state in which the band body 100 is worn on the wrist H, the compression pads 200, i.e. the radial compression pad 210 and the ulnar compression pad 220, compress the radial part H1 and the ulnar part H2 of the wrist H in opposite directions, from the outside toward the center of the wrist H.

Here, the wrist guard 10 is configured so as not to compress the wrist other than those compressed by the compression pads 200. That is, the wrist H is not compressed by the band body 100, except for the portion of the wrist H compressed by the compression pads 200. Although a portion of the band body 100 may contact the wrist H depending on the thickness of the compression pad 200, the magnitude of the tension of the band body 100 surrounding the wrist H, the outer shape of the wrist H, and the like. In this case, the band body 100 is simply in contact with the wrist H without compressing the wrist, and even if applied, the contact pressure is very small compared with the compression force applied by the compression pads 200. Accordingly, the contact pressure may be deemed to be ignorable.

As described above, the wrist guard 10 is configured such the compression pads 200 compress the radial part H1 and the ulnar part H2 of the wrist H to complement the fixing force for the wrist H, thereby preventing excessive bending of the wrist H and relieving the pain of the wrist. Thus, the wrist protection function can be reliably performed. Here, other parts of the wrist are not compressed, except for the radial part H1 and the ulnar part H2 compressed by the compression pads 200, so that the blood circulation is not disturbed, and thus, side effects such as numbness and swelling of hands do not occur.

Meanwhile, a health aid 300 may be inserted into the compression pads 200 so that various health-aid effects may be provided to the wrist region. Here, the health aid may be formed of zirconium (Zr), germanium (Ge) or the like.

The compression pads 200 may be provided in various shapes as illustrated in FIG. 4. For example, as illustrated in FIG. 4A, the length L1 of the radial compression pad 210 may be provided to be longer than the length L2 of the ulnar compression pad 220. The bones that make up the arms include the radial part H1 and the ulnar part H2, which protrude outwardly from the wrist H. Here, the radial part H1 is thicker than the ulnar part H2 and has a wider area of protrusion than the ulnar part at the wrist H. Since the radial part H1 has a relatively larger area than the ulnar part in the wrist region, it may be preferred that the radial compression pad 210 is provided to be longer than the ulnar compression pad 220 to effectively compress the radial part H1 and the ulnar part H2.

The protruding portions of the radial part H1 and the ulnar part H2 in the wrist H are not symmetrically opposed to each other but are slightly displaced. Thus, the radial compression pad 210 and the ulnar compression pad 220 may be disposed in positions offset from the center line L1 passing through the center C of the ring-shaped band body 100 as illustrated in FIG. 4B. That is, the center C1 of the radial compression pad 210 may be located on the center line L1 of the band body 100 and the center C2 of the ulnar compression pad 220 may be located at a predetermined rotation angle from the center line L1 of the band body 100.

Further, as illustrated in FIG. 4C, the compression pads 200 may be provided to have a concave surface to be brought into contact with the wrist H at a longitudinally intermediate portion thereof. That is, in a case in which the compression pad 200 is provided to have a uniform thickness, the contact surface with respect to the wrist H is provided along the line S1 parallel with the curved line of the band body 100, whereas in an exemplary embodiment of the present disclosure, the contact surface with respect to the wrist H may be provided along the line S2 in a concavely curved shape. Since the contact surface with the wrist H is concavely curved so that the compression pads 200 can be more closely attached to the wrist H so as to more firmly compress the radial part and the ulnar part of the wrist H.

Figure 6:
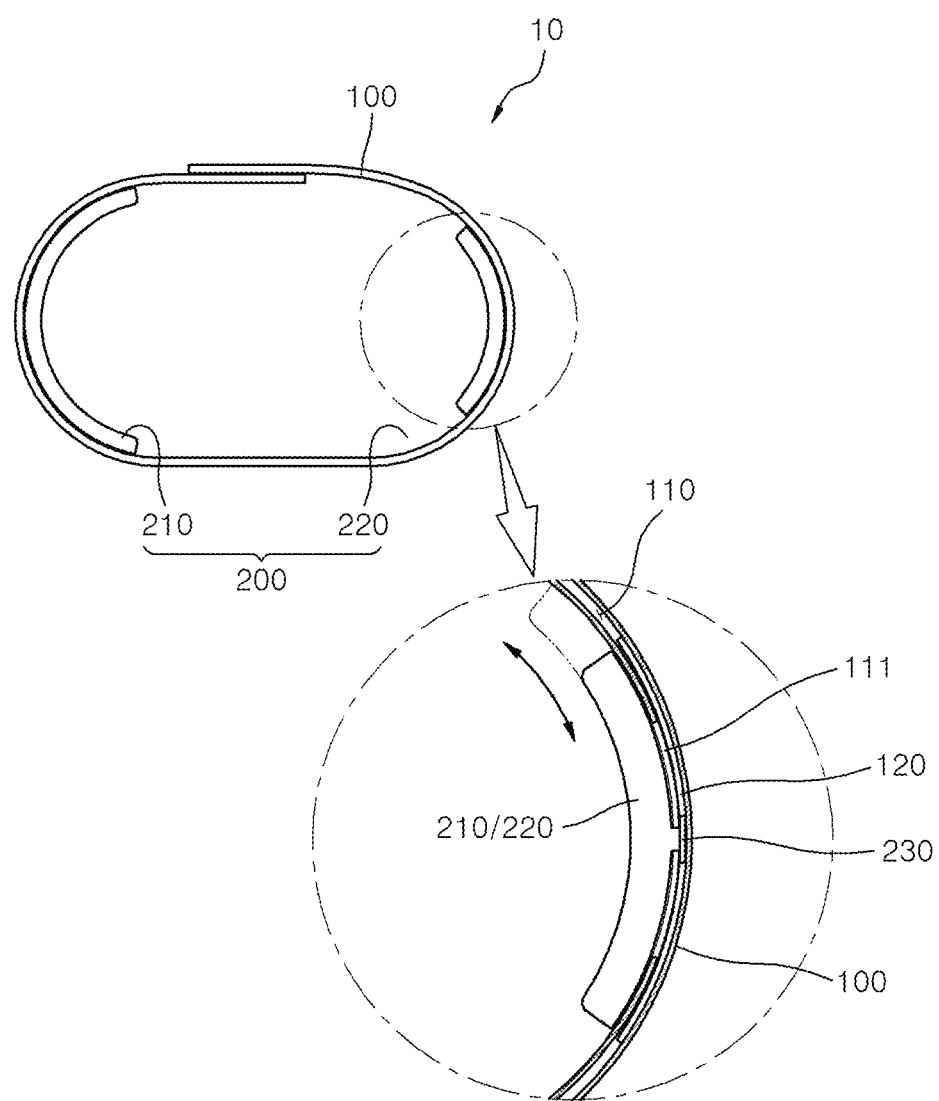

FIGS. 5 and 6 are views schematically illustrating a structure of the compression pad moving along the band body according to an exemplary embodiment of the present disclosure.

As illustrated in FIGS. 5 and 6, the compression pads 200 may be mounted to move along the longitudinal direction of the band body 100 by a predetermined interval to adjust the mounting positions of the compression pads 200, thereby precisely compressing the radial and ulnar parts, which may be located in positions that are different from user to user.

When the band body is worn on the wrist H, the compression pads 200 compress the radial part H1 and the ulnar part H2 of the wrist H in opposite directions. Here, since the shape of the wrist H, positions of the radial part H1 and the ulnar part H2, and the like may differ slightly from person to person, the compression pads 200 may not compress the correct points of the wrist depending on the user.

Therefore, by allowing the user to move and adjust the compression pads 200 to proper positions, the compression pads 200 can be positioned at the correct positions so as to precisely compress the radial part H1 and the ulnar part H2.

For the movement of the compression pads 200, a contact surface of each of the compression pad 200 with the band body 100 may be provided with an insertion protrusion 230, and the band body 100 may be provided with a pad receiving section 110 in which the insertion protrusion 230 is inserted and movable, wherein the pad receiving section 110 internally has a movement guide part 120 along which the insertion protrusion 230 is forcedly movable in a state of being engaged therewith. Here, as illustrated in FIGS. 5 and 6, the band body 100 is formed of a double-layer structure including an inner layer and an outer layer between which the pad receiving section 110 is provided. The inner layer may be provided at the center thereof with a cutout portion 111, which extends along the longitudinal direction of the inner layer so that the pad receiving section 110 is opened. The insertion protrusion 230 is inserted and received in the pad receiving section 110 through the cutout portion 111 and is movable in the longitudinal direction along the movement guide part 120 disposed inside the pad receiving section 110. The movement guide part 120 may be provided on opposite lateral sides with concavo-convex portions 121 along which the insertion protrusion 230 is forcedly movable divisionally in a state of being engaged therewith.

According to this configuration, in a state where the user wears the band body 100 on the wrist H, the position of the compression pads 200 can be adjusted by pushing or pulling the compression pads 200 along the longitudinal direction, thereby enabling the radial part and the ulnar part to be precisely compressed.

Figure 7:
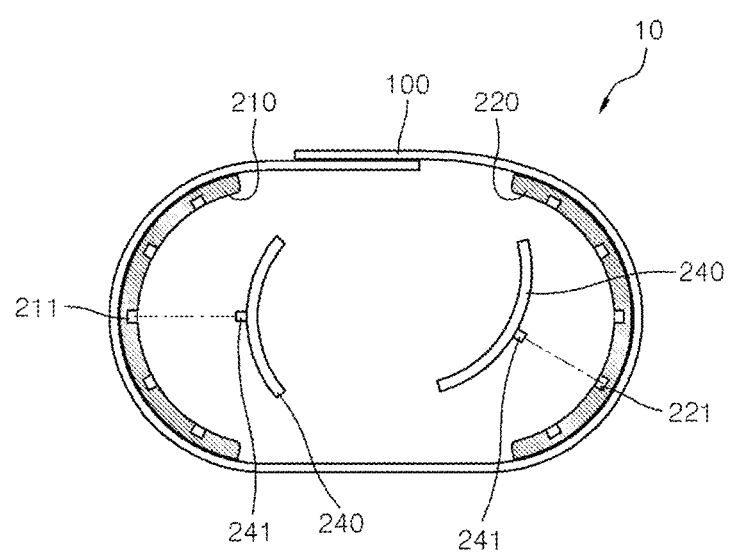
FIG. 7 is a schematic view illustrating an engagement structure of an auxiliary compression pad with the compression pad of the wrist guard according to an exemplary embodiment of the present disclosure.

FIG. 7 is a schematic view illustrating an engagement structure of an auxiliary compression pad with the compression pad of the wrist guard according to an exemplary embodiment of the present disclosure.

As illustrated in FIG. 7, the compression pad 200 may be further provided with a separate auxiliary compression pad 240.

The auxiliary compression pad 240 may be configured to be detachably attached to a contact surface of the radial or ulnar compression pad 210 or 220 with the wrist H. The auxiliary compression pads 240 are engaged with the contact surfaces of the radial compression pad 210 and the ulnar compression pad 220 with respect to the wrist H so as to substantially compress the radial part H1 and the ulnar part H2 of the wrist H. The auxiliary compression pad may be formed of a soft material such as leather or silicone as in the case of the radial compression pad 210 and the ulnar compression pad 220.

The thickness of the compression pads 200 can be adjusted by attaching or removing the auxiliary compression pads 240 to or from the radial compression pad 210 and the ulnar compression pad 220. That is, when the auxiliary compression pads 240 are respectively attached to the radial compression pad 210 and the ulnar compression pad 220, the thickness of the compression pads 200 become thicker as a whole, whereas when the auxiliary compression pads 240 are respectively removed from the radial compression pad 210 and the ulnar compression pad 220, the thickness of the compression pads 200 become thinner as a whole.

As a result, the entire thickness of the compression pads 200 can be adjusted by using the auxiliary compression pads 240, so that a user can adjust the thickness of the compression pads 200 to an appropriate thickness depending on his/her physical condition, an environmental condition, or the like.

Here, a contact surface of the radial compression pad 210 and the ulnar compression pad 220 with respect to the wrist H may be provided with coupling grooves 211, 221, and the auxiliary compression pads may be provided on one portion thereof with coupling protrusions 241 to be inserted into and engaged with the coupling grooves 211, 221, so that the auxiliary compression pads 240 are detachably attached to the radial compression pad 210 and the ulnar compression pad 220, respectively, by the engagement between the coupling grooves 211, 221 and the coupling protrusions 241.

Further, the coupling groove may be provided with a plurality of coupling grooves 211, 221 in the longitudinal direction of the radial compression pad 210 and the ulnar compression pad 220 in order to substantially adjust an engagement position of the auxiliary compression pads 240 with the radial compression pad and the ulnar compression pad.

That is, as illustrated in FIG. 7, the coupling protrusion 241 of the auxiliary pressing pad 240 is selectively coupled to any one of the coupling grooves 211 and 221 of the radial compression pad 210 and the ulnar compression pad 220, so that the engagement position of the auxiliary compression pad 240 can be adjusted and the compression position of the auxiliary compression 240 with respect to the wrist H can thus be conveniently adjusted.

The foregoing descriptions have been presented in order to explain certain principles of the present disclosure by way of example. A person skilled in the art to which the present disclosure relates could make various modifications and variations without departing from the essential features of the present disclosure. The foregoing embodiments disclosed herein shall be interpreted as being illustrative, while not being limitative, of the principle and scope of the present disclosure. It should be understood that the scope of the present disclosure shall be defined by the appended Claims and all of their equivalents fall within the scope of the present disclosure.

The invention claimed is:

1. A wrist guard for being worn on a wrist to protect the wrist, the wrist guard comprising:
  a band body configured to be worn on the wrist by encircling the wrist; and
  a pair of compression pads disposed on opposite portions of the band body worn on the wrist for compressing a part of the wrist,
  wherein the compression pads include a radial compression pad mounted on one portion of the band body for compressing the radial part of the wrist and an ulnar compression pad mounted on another portion of the band body for compressing the ulnar part of the wrist, the compression pads being mounted to be movable in a longitudinal direction of the band body,
  wherein
  a contact surface of each compression pad which contacts the band body is provided with an insertion protrusion,
  the band body is formed of a double-layer structure including an inner layer and an outer layer between which a pad receiving section is provided, the pad receiving section internally having a movement guide part,
  the inner layer is provided at the center thereof with a cutout portion, which extends along the longitudinal direction of the inner layer so that the pad receiving section is opened,
  the insertion protrusion is inserted and received in the pad receiving section through the cutout portion and is movable in the longitudinal direction along the movement guide part disposed inside the pad receiving section, and
  the movement guide part is provided on opposite lateral sides with concavo-convex portions along which the insertion protrusion is forcedly movable in a state of being engaged therewith.

2. The wrist guard according to claim 1, wherein the radial compression pad has a length (L1) longer than a length (L2) of the ulnar compression pad.

3. The wrist guard according to claim 1, wherein at least one of the radial compression pad or the ulnar compression pad has a concave surface to be in contact with the wrist in a longitudinally intermediate portion thereof.

4. The wrist guard according to claim 1, wherein the radial compression pad and the ulnar compression pad respectively further include a separate auxiliary compression pad detachably attached for contacting a surface thereof with the wrist.

5. The wrist guard according to claim 4, wherein the contact surfaces of the compression pad and the ulnar compression pad is provided with a coupling groove, and the auxiliary compression pad is provided on one portion thereof with a coupling protrusion to be inserted into and engaged with the coupling groove, so that the auxiliary compression pads are detachably attached to the radial compression pad and the ulnar compression pad, respectively, by the engagement between the coupling groove and the coupling protrusion.

6. The wrist guard according to claim 5, wherein the coupling groove is provided with a plurality of coupling grooves in a longitudinal direction of the radial compression pad and the ulnar compression pad to adjust an engagement position of the auxiliary compression pads with the radial compression pad and the ulnar compression pad.

7. The wrist guard according to claim 1, wherein the compression pads are formed from a leather or silicone material.

8. The wrist guard according to claim 7, wherein the compression pads are further provided with a health aid to be inserted into the compression pads, the health aid being formed of zirconium or germanium.

9. The wrist guard according to claim 1, wherein the band body is provided in the form of an elastic ring band, or a band fixedly formed into a ring type by means of a fastener.

10. The wrist guard according to claim 2, wherein the compression pads are formed from a leather or silicone material.

11. The wrist guard according to claim 3, wherein the compression pads are formed from a leather or silicone material.

12. The wrist guard according to claim 2, wherein the band body is provided in the form of an elastic ring band, or a band fixedly formed into a ring type by means of a fastener.

13. The wrist guard according to claim 3, wherein the band body is provided in the form of an elastic ring band, or a band fixedly formed into a ring type by means of a fastener.

\* \* \* \* \*